United States Patent [19]

Brandly et al.

[11] Patent Number: 6,087,830

[45] Date of Patent: *Jul. 11, 2000

[54] FLEXIBLE DEVICE FOR REMOTE FIELD EDDY CURRENT INSPECTION OF FERROUS PIPELINE CONTAINING TURNS

[75] Inventors: Gordon R. Brandly, Edmonton; Martin D. MacLean, Ardrossan; Paul P. Pastushak, Edmonton; David E. Russell, Sherwood Park; James B. Seale, Edmonton; Ad A. Shatat, Edmonton; Jens C. B. Winslow, Edmonton, all of Canada

[73] Assignee: Hydroscope Canada Inc., Edmonton, Canada

[*] Notice: This patent is subject to a terminal disclaimer.

[21] Appl. No.: 08/941,057

[22] Filed: Sep. 30, 1997

Related U.S. Application Data

[63] Continuation-in-part of application No. 08/271,713, Jul. 7, 1994, Pat. No. 5,675,251.

[51] Int. Cl.[7] .......................... G01N 27/72; G01N 27/82; G01R 33/12

[52] U.S. Cl. ............................. 324/220; 324/240

[58] Field of Search .................... 324/219, 220, 324/221, 226, 262, 240; 23/623, 638

[56] References Cited

U.S. PATENT DOCUMENTS

| | | |
|---|---|---|
| 2,573,799 | 11/1951 | MacLean . |
| 2,992,390 | 7/1961 | DeWitte . |
| 3,060,377 | 10/1962 | Schmidt . |
| 3,243,697 | 3/1966 | Schmidt . |
| 3,417,325 | 12/1968 | Mc Cullough . |
| 3,532,969 | 10/1970 | Mc Cullough . |
| 4,292,588 | 9/1981 | Smith . |
| 4,292,589 | 9/1981 | Bonner . |
| 4,372,161 | 2/1983 | de Buda et al. . |
| 4,546,314 | 10/1985 | Minerbo . |
| 4,621,532 | 11/1986 | Takagi et al. . |
| 4,633,177 | 12/1986 | David et al. . |
| 4,644,272 | 2/1987 | Janos . |
| 4,770,105 | 9/1988 | Takagi et al. . |
| 4,808,924 | 2/1989 | Cecco . |
| 4,808,927 | 2/1989 | Cecco . |
| 4,855,676 | 8/1989 | Cecco . |
| 4,866,978 | 9/1989 | Biggerstaff . |

(List continued on next page.)

OTHER PUBLICATIONS

"Remote Field Eddy Current for Examination of Ferromagnetic Tube"—technical paper by D.D. Mackintosh, D.L. Atherton, T.R. Schmidt and D.E. Russell; Reprinted from: *Materials Evaluation*, vol. 54, No. 6, pp: 652–657, The American Society for Nondestructive Testing, Inc.

"Remote Field Eddy Current Examination of Boiler Tubes"—technical paper by H. Smith and D. Mackintosh of Russell Technologies Inc., Edmonton, Alberta, Canada; From Proceedings of the EPRI Topical Workshop: Electromagnetic NDE Application in the Electric Power Industry, Charlotte, NC, Aug. 21–23 1995.

(List continued on next page.)

*Primary Examiner*—Walter E. Snow
*Attorney, Agent, or Firm*—Christensen O'Connor Johnson Kindness PLLC

[57] ABSTRACT

A device is taught for inspecting the integrity of water distribution pipelines. The device is constructed of housing units, for housing inspection circuitry. The housing units are connected by flexible connectors which permit the units to move out of axial alignment to pass bends. In some embodiments, communication ports are provided between the units. As such, the device is able to negotiate bends and pass through openings of reduced size in the pipeline. The device can be used with various inspection technologies including remote field eddy current inspection technology. A method for inspecting the integrity of a water pipeline system is disclosed wherein water hydrants can be used to access the system.

54 Claims, 8 Drawing Sheets

U.S. PATENT DOCUMENTS

| | | |
|---|---|---|
| 4,945,775 | 8/1990 | Adams et al. . |
| 5,049,817 | 9/1991 | Cecco . |
| 5,204,622 | 4/1993 | McCaslin et al. . |
| 5,210,492 | 5/1993 | Hosohara et al. . |
| 5,214,379 | 5/1993 | Chern . |
| 5,313,838 | 5/1994 | Gondard et al. . |
| 5,329,824 | 7/1994 | Carapezza et al. . |
| 5,365,169 | 11/1994 | Hosohara et al. . |
| 5,365,331 | 11/1994 | Tamburrino et al. . |
| 5,398,560 | 3/1995 | Zollingger et al. . |
| 5,402,065 | 3/1995 | Tabari et al. . |
| 5,453,688 | 9/1995 | Cecco et al. . |
| 5,454,276 | 10/1995 | Wernicke . |
| 5,461,312 | 10/1995 | Hosohara et al. . |
| 5,461,313 | 10/1995 | Bohon et al. . |
| 5,532,587 | 7/1996 | Downs et al. . |
| 5,623,203 | 4/1997 | Hosohara et al. . |
| 5,640,780 | 6/1997 | Kermabon . |

OTHER PUBLICATIONS

"Hydroscope Provides Water Line Asset Management", Trenchless Technology, Mar. 1997.

Russell, D.E. and Davies A.T., "New Tools for Water Main Asset Management", No–Dig Engineering, 3rd Quarter 1997.

"CERF Conducts New Technology Evaluation for the Public Works Community" CERF Currents, vol. 97.3, Fall 1997.

Staples, L.B. "A New Tool for Condition Evaluation of Cast and Ductile Iron Pipe". NACE Corrosion 96. Denver, Colorado, Mar. 1996. pp. 45/1–45/9.

Russell, D.E. and Davies A.T., "Condition Evaluation Technology for Water Main Asset Management", AWWA Annual Conference. Atlanta, Georgia, Jun. 1997.

Ferguson, P. et al., "Condition Assessment of Water Mains Using Remote Field Technology", Water, Apr. 1996, pp. 6–8.

Winslow, Jens C., "High Resolution Detectors for Remote Field Eddy Current Probes", Queen's University, Dept. of Physics, Kingston, Canada, M.Sc. Thesis 1995.

Winslow, J. C. and Atherton, D.L., "High Resolution Detectors for Remote Field Eddy Current Probes", CSNDT Journal, vol. 16, No. 5 (Sep./Oct. 1995), pp. 8, 10–13, 22–25.

Staples, L.B., "New Tools for the Condition Evaluation of Waterlines", Centre d'expertise et de Recherche en Infrastructure Urbanes. Montreal, Quebec, Sep. 1995.

Koutsakos, E. et al, "Using a non–destructive technique for evaluating water mains conditions", 3rd International Conference on Water Pipeline Systems. BHR Group Conference Series, Publication No. 23 ed. Chilton, R. May 1997, pp. 93–105.

Schmidt, T.R., "History or Remote Field Eddy Current Inspection Technique", 1989.

"Non–Destructive Testing of Water Mains for Physical Integrity", AWWA Research Foundation and American Water Works Assoc., 1992.

Ferguson, P.H., M.J. Heathcote, G. Moore and D.E. Russell, 1996. Condition Assessment of Water Mains Using Remote Field Technology. *Water.* Mar./Apr. 1996, pp. 6–8.

Koutsakos, E., T. Woodward and D.E. Russell, 1997. Using a Non–destructive Technique for Evaluating Water Mains Conditions. 3rd International Conference on Water Pipeline Systems, BHR Group Conference Series, Publication No. 23, edited by R. Chilton. May 1997, pp. 93–105.

Russell, D.E. and A.T. Davies, 1997. Condition Evaluation Technology for Water Main Assest Management. AWWA Annual Conference, Atlanta Georgia. Jun. 1997.

Staples, L.B., 1994. New Tools for the Condition Evaluation of Waterlines. Seminar on Trenchless Technology: Underground Infrastructure—the Sick Waiting to be Diagnosed. Centre d'expertise et de Recherché en Infrastructure Urbanes, Montréal, Québec. Dec. 1994.

Staples, L.B., 1996. A New Tool for Condition Evaluation of Cast and Ductile Iron Pipe. NACE Corrosion 96, Denver, Colorado. Mar. 1996, pp. 45/1–45/9.

Tenove, Ron, 1997. Hydroscope Provides Water Line Asset Management. *Trenchless Technology*, Mar. 1997, pp. 40–42.

FLEXIBLE DEVICE FOR REMOTE FIELD EDDY CURRENT INSPECTION OF FERROUS PIPELINE CONTAINING TURNS

CROSS-REFERENCE TO RELATED APPLICATIONS

The present application is a continuation-in-part of U.S. application Ser. No. 08/271,713 filed Jul. 7, 1994, now U.S. Pat. No. 5,675,251.

FIELD OF THE INVENTION

The present invention relates to a method and device for inspection of pipelines and, in particular, the present invention relates to a method and device for inspection of the physical integrity of water distribution pipelines.

BACKGROUND OF THE INVENTION

Many water distribution systems throughout the world have been in use for periods approaching or exceeding a century. Over time, the water systems have received varying degrees of maintenance. However, inspection is difficult without costly excavation. Often, no action is taken until a leak is detected, at which time the section surrounding the leak is excavated and repaired. System maintenance has often been limited to monitoring the failure rates for individual lines and performing replacement of an entire line or a long segment of it when leak frequency has exceeded tolerable values. This approach may lead to unnecessary replacement of considerable good pipe. As a result, there exists a need for a cost effective method to ascertain line condition. Since water lines are almost always buried, any applicable inspection method must be capable of operating solely within the bore of the pipe, to detect flaws such as corrosion and cracks through the entire thickness of the pipe.

In order to make inspection cost effective, it must be possible to perform the inspection with minimal preparation of the line, and, in particular, without having to excavate the lines. This means that the inspection device must be capable of accessing the line through existing access points, such as hydrants. The pipes are designed to operate under high internal pressures of, for example, up to 350 PSI. In general, however, the water pressure will be much lower due to operational constraints such as service connections, bell and spigot connections and dead ends. The inspection device must be able to withstand and to operate in such water pressures.

The inspection method must be useable with pipes made of inhomogeneous materials, such as cast iron. In addition, the inspection apparatus must be capable of operating in an environment having the presence of right-angle elbows and tees, large numbers of service taps and fittings, and the relatively large accumulations of scale typical of municipal water systems.

There are several methods of inspection which offer the possibility of measuring pipe condition from the inside, and which are used for this purpose in other applications. Among these are audio inspection, ultrasonic, magnetic flux leakage, eddy current, and remote field eddy current technology.

Ultrasonic methods are used extensively to measure the thickness of many materials with one sided access only, and exhibit very good accuracy in most steels. Unfortunately, they do not work well in cast iron, because the grain size in cast iron approaches the ultrasonic wave length. This results in severe scattering and attenuation of the acoustic signal.

Flux leakage methods are used extensively in oil well casing and petroleum pipeline applications. They are limited by the requirements that the pipe be very clean inside to obtain good flux coupling and to prevent sensor bounce, and that a substantially constant speed be maintained. The scale build-up typical of water lines prevents flux leakage inspection, as does the relatively great wall thickness of these lines. In addition, while this method is effective for the detection of localized sharp edged pits and cracks, it is insensitive to general overall wall loss.

Eddy current methods have been the technique of choice for many years in the inspection of non-magnetic metal piping in applications such as air conditioning units and non-ferrous chemical process piping. These methods use high frequency sinusoidal varying electromagnetic energy and measure the effects of the pipe wall thickness on the field generated by the exciter. In magnetic materials such as cast irons and carbon steels, the depth of penetration of eddy currents is greatly reduced, precluding inspection of the outside of the pipe, particularly when the pipe is of appreciable thickness. Attempts have been made to overcome this limitation by the use of constant magnetic fields to reduce the effective magnetic permeability of the material, but the thickness of typical water lines and the presence of scale make this method impractical for the inspection of these lines. Also, eddy current probes react strongly to changes in the distance between the sensors and the material under inspection, which requires that the inside of the pipe be very clean. For these reasons, this is not a viable method for water line applications.

Remote field eddy current (RFEC) is a relatively new electromagnetic inspection method which has become prominent in the last few years. The term "remote field eddy current" is used to describe the technique in which an alternating magnetic field induced in the pipe by a means such as an exciter or source coil and the field, as modified by the pipe material, is detected at a detector. The detector must be spaced from the exciter coil a sufficient distance to eliminate direct coupling within the pipe between the exciter coil and the detector, and thereby overcome the problems associated with traditional eddy current methods. From classic eddy current equations one can derive an equation illustrating that flux density at any depth will be attenuated and delayed in time (shifted in phase) in a manner related to metal thickness. In particular, eddy current instruments detect a flaw by measuring the reduced attenuation, time delay and field direction the flaw produces as compared with a normal wall thickness. This perturbation in the inner wall electromagnetic field pattern caused by a flaw is highly localized in the vicinity of the flaw and will, to a limited extent, outline the shape of the flaw.

SUMMARY OF THE INVENTION

The present invention provides a method and apparatus for inspection of water distribution pipelines. The apparatus preferably uses RFEC technology which permits the physical integrity on both the inside and outside of a pipe to be ascertained without requiring access to the exterior of the pipe.

According to a broad aspect of the present invention, there is provided a remote field eddy current inspection device for water pipelines comprising:

(a) an exciter unit housing an exciter means for producing a time-varying magnetic field in response to an exciting signal;

(b) a detector unit housing at least one detector means for producing a detecting signal representative of the time-varying magnetic field proximal to said detector means and resulting from the exciter means; and, (c) an elongate flexible connector spacedly connecting the exciter unit to the detector unit, the elongate flexible connector being selected to space the exciter means from the detector means a distance suitable for measurement of the remote field eddy current effect.

According to another broad aspect of the present invention there is provided a remote field eddy current inspection device for water pipelines comprising:

(a) an exciter unit housing an exciter means for producing a time-varying magnetic field in response to an exciting signal;

(b) a first detector unit housing at least one first detector means for producing a first detecting signal representative of the time-varying magnetic field proximal to said first detector means and resulting from the exciter means;

(c) a second detector unit housing at least one second detector means for producing a second detecting signal representative of the time-varying magnetic field proximal to said second detector means and resulting from the exciter means;

(d) an elongate flexible connector spacedly connecting the exciter unit to the first detector unit, the elongate flexible connector being selected to space the exciter means from the first detector means a distance suitable for measurement of the remote field eddy current effect;

(e) an elongate flexible connector spacedly connecting one of the exciter unit and the first detector unit to the second detector unit, the elongate flexible connector being selected to space the exciter means from the second detector means a distance suitable for measurement of the remote field eddy current effect.

According to a further broad aspect of the present invention, there is provided a remote field eddy current method for inspecting water pipelines comprising:

(a) moving an inspection device through pipeline using a moving means, wherein the inspection device includes an exciter unit housing an exciter means, a detector unit housing at least one detector means and an elongate flexible connector spacedly connecting the exciter unit to the detector unit, the elongate flexible connector being selected to space the exciter means from the detector means a distance suitable for measurement of the remote field eddy current effect;

(b) inducing a time-varying magnetic field in the pipeline with the exciter means in response to an exciting signal;

(c) producing a detecting signal representative of the magnetic field proximal to the detector means and resulting from the exciter means;

(d) producing data representative of at least one of (i) the phase and amplitude and (ii) the in-phase and quadrature, of the detecting signal.

According to yet another broad aspect of the present invention, there is provided a remote field eddy current inspection device for water pipelines comprising: an exciter unit housing an exciter means for producing a time-varying magnetic field in response to an exciting signal and spacedly connected thereto a detector unit housing at least one detector means for producing a detecting signal representative of the time-varying magnetic field proximal to said detector means and resulting from the exciter means, the detector means includes an outer ring of spot coils disposed to measure the radial component of the magnetic field and an inner ring of spot coils disposed to measure the radial component of the magnetic field, the rings of coils being positioned at substantially the same position along the axis of the device and the outer ring of coils being disposed between an outer wall of the device and the inner ring of coil, each coil in the outer ring of coils being positioned such that its axis is substantially aligned with the axis of one coil from the inner ring of coils.

DESCRIPTION OF THE INVENTION

A device is provided for inspecting the integrity of water distribution pipelines by moving along the inner bore of the pipelines. The device can be used with RFEC, and various other inspection technologies. The device is able to negotiate the hydrants, tees, elbows and valves encountered in such a pipeline due to its "balls-on-a-string" design. The "balls" are a plurality of housing units in series, while the string is a flexible connector which extends between each consecutive housing unit in series.

The housing units house the exciter, the detector and the internal circuitry of the device. As such, the housing units are sealed to prevent the entry of water into the unit. Preferably, the units are formed of high strength, waterproof, pressure resistant and abrasion resistant materials such as, for example, the thermoplastics Delrin™ or Nylatron™, stainless steel and/or similar materials. The units are sealed by means of O-rings, gaskets and the like or, alternatively, by use of tapered thread fittings or welding. To facilitate the movement of the device along the pipeline, each housing unit is of a size suitable for passing through the pipeline bore. As an example, a housing having a diameter of 4" is preferred for use in the 6" (internal diameter) pipe commonly used in water distribution lines. In addition, the housing units are shaped to be stream-lined. Preferably, the leading end of the housing units are generally rounded or have attached thereto centralizers such that they will not catch on joints, corners or discontinuities along the pipe bore. Preferably, both the leading end and the trailing end of each housing unit are shaped to facilitate the entry of the device into the pipe as well as the removal of the device along the same path.

To facilitate the negotiation of tees and elbows in the pipeline, the housing units should be compact and, thus, will carry a limited amount of circuitry in each unit. In the preferred embodiment, circuitry is positioned within the units in engagement with a central shaft by means of mechanical spacers and screws which provides for easy assembly. The number of units used, then, will relate to the amount of circuitry incorporated in the device and the space requirements of the circuitry. Any number of units can be strung together to form the device.

To facilitate the negotiation of bends in the pipeline by the device, the units are mounted together with flexible connectors, such that they are able to move out of alignment with each other. Examples of suitable flexible connectors are wire, rope, shafts having pivotally moveable joints or tubing. Where communication is required between the units, such as for electrical connection, wires, sealed against the entry of water, can be extended between the units. The wires can be disposed within a flexible tubular element which is attached between the housing units to maintain the seal against water. Preferably, the tubular element is a stainless steel jacketed, Teflon™ lined hydraulic-type hose with threaded pressure connectors for attachment to the housing units. The seal is maintained at the connection by use of a tapered thread design along with the use of Teflon™ tape or the like, if desired. The length of the connector between each unit is sufficient to allow the device to flex around bends which is generally equivalent to about 0.8 to 3.5 pipe bore diameters.

The device can be fitted with anchor means for connection to lines at the leading and trailing end of the device. The connection can be to a pulling line for moving the device along the pipe by any suitable moving means, such as an above-surface pulling means, a pulling pig, a pipe wall engaging driving means or a propeller. In addition, the connection can include a sealed flexible connector as is used between housings to allow communication to the surface, such as for power or data transmission. Alternatively, a wireline having an outer armour can be used for data transmission and power supply. Such a wireline can also be used as the moving means.

To make use of the defect information collected by the device, it is sometimes necessary to use device locating means. Suitable device locating means are, for example, timers and/or displacement sensors, such as odometers or accelerometers, attached to the wireline or the device. A means for locating the device can also be provided by marking any attached lines.

In use, the device is fed into a pipeline system through an access point such as a hydrant or a hot tap. Alternately, a hydrant adapter can be used as the access point. A hydrant adapter is a hydrant-like structure which is mountable onto an access port in a water line. Preferably, the access point is a hydrant, thereby avoiding excavation. Where a pulling line is used with the device, the pulling line is fed into the hydrant and pulled through the pipeline by means of a pulling pig which is driven by water or air pressure.

The device moves along the pipeline by the desired moving means and inspects the pipeline. The data collected can be stored internally of the housing units or transmitted to the surface for real time analysis.

Pipelines of any length can be inspected. However, where trailing or pulling lines are used, limitations in the lengths of the lines which are available may limit the length of the pipeline which can be inspected. The pipeline is preferably first cleaned of rust and debris by use of a scraper pig or brush. This facilitates inspection and movement of the device along the pipeline. The section of pipe to be inspected can be sealed off or alternatively, can contain flowing fluid.

A device which uses RFEC for inspection will include a unit housing an exciter means. The exciter means generates the requisite time-varying electromagnetic field, for example a sinusoidally varying field or pulsed field, for use in RFEC inspection. Suitable exciter means can be, for example, a permanent magnet disposed to be rotated or, preferably, an exciter coil.

Many exciter coil arrangements are useful as the exciter means. For example, a single axial (i.e. disposed in the device to produce an axial magnetic field), fully circumferential (i.e. having a diameter substantially equal to the diameter of the tool) coil or one or more spot coils (i.e. a coil sized such that more than one coil can be accommodated at the same position along the axis of the device: also known as a segmented coil) for producing a radial magnetic field disposed in a ring about the circumference of the device. The exciter coil in combination with the detector means, which will be described hereinafter, must be selected to generate a field which is sufficient to generate at least about a 1 micro V signal at the detector. Many combinations of wire gauge, number of turns, size and orientation are possible. In the preferred embodiment, there is provided a single, full circumferential, axial exciter coil consisting of 270 turns of #26 wire, with coil width and depth being equal and resistance being 9.2 ohms. The exciter is driven by a power source such as, for example, a source of alternating current which is connected to the device through a wireline. Alternatively, the exciter coil is driven by a battery and oscillating circuitry means contained within the unit, or by any other suitable power sources. Preferably, a power-on delay circuit is provided to delay the application of power to the exciter coil until the voltage of applied power has reached an appropriate level.

The unit housing the exciter coil, which will be referred to herein as the exciter unit, is fitted with centralizers which act to maintain the concentric positioning of the unit within the bore of the pipe and to limit the abrasion of the unit. Centralizers can include, for example, rods, brushes or outwardly biased wheels or skids. The centralizers are formed of durable, resilient material. In a preferred embodiment, the centralizers are polyurethane loops. Such centralizers have been found to move along the pipe bore smoothly, substantially without generating noise and are bendable to pass through areas of reduced diameter. The loops are selected such that they are rigid enough to support the weight of the device or unit to which they are attached but are flexible enough to substantially avoid drag and to permit the device to manoeuvre around pipe corners. Polyurethane loops formed from ⅛" thick polyurethane sheet material are preferred. The polyurethane loops can be reinforced with Kevlar™ cloth or ceramic balls to increase their wear resistance.

The exciter unit is connected by a flexible connector to at least one unit, which will be referred to herein as the detector unit. The detector unit houses at least one detector means which detects the magnetic field arriving at the detector resulting from the exciter means. According to RFEC principles, the detector means must be spaced from the exciter means by a distance suitable to measure the RFEC effect, the effect being the perturbation of the magnetic field caused by passing through the pipe wall twice. As an example, where the exciter means generates a sinusoidally varying field, the detector means must be separated from the exciter means by a length of at least about 2× the internal diameter of the pipe. The detector can be either partially or fully circumferential, or a combination of the two geometries. Suitable detector means include those constructed from solid state detectors, such as hall-effect or magnetoresistive sensors, and/or coils suitably arranged such as, for example, one or more coils disposed to measure the axial field, one or more coils disposed to measure the radial field and/or one or more coils disposed to measure the circumferential field. Tipped coils can also be used which are capable of measuring combinations of the axial, circumferential and radial fields. The coils can be radially, axially and circumferentially aligned. Many combinations of wire gauge, number of turns and size are possible for the detector coils. Preferably, the detector coil arrangement includes at least one full circumferential, axial coil.

The coils in the detector can be fitted with cores. Since electrically conductive materials tend to oppose the magnetic field which is sought to be detected, such cores are formed preferably from materials that are not electrically conductive. Preferably, the cores are formed of materials having high magnetic permeability (high $\mu$) such as, for example, ferrite or metglass. Cores of high permeability are conducive to the magnetic field and attract field into the detector coil to increase the local flux density. In coils having such cores, the detector signal will be boosted. The cores of the coils can be of any suitable shape, for example, disc or U-shaped. Spot coils having U-shaped cores have been found to provide better signal to noise ratio. Shields, for example metal cups, can be positioned about the coils to remove background signals.

The detector means should preferably be arranged within the detector unit to be as close to the pipe wall as possible. This can be accomplished by enlarging the unit or by mounting the detectors in the centralizers.

Preferably, the signal detection is accomplished by a plurality of detector coils of different types including full circumferential and smaller spot coils. The use of combinations of detector coils permits greater defect analysis in a single inspection run.

In one embodiment of a device for a pipe of 6" diameter, the detector coil group includes two full circumferential coils each consisting of 7,000 turns of #40 copper wire with coil length being equal to coil depth and a resistance of 4.8 kOhms and four smaller spot coils each consisting of 7,000 turns of #43 wire with a resistance of 7.0 kOhms. The spot coils are arranged in the device such that they are spaced apart evenly about the circumference of the device and are positioned with their axes parallel to the axis of the pipe. In this embodiment, the spot coils are D-shaped having a flat side adjoining a rounded side. The rounded side is selected such that its curvature conforms substantially to the curvature of the pipe into which the tool is to be used. The coils are positioned end to end about the circumference of the device. Such coils improve the sensitivity of the system to small anomalies in the pipe which is inspected.

In another embodiment, the detector coil group includes a plurality of spot coils selected to be about the same size as or smaller than the smallest defect which is desired to be detected and positioned such that their axes are aligned with the radius of the pipe.

Each of the detector coils produces detector signal which is coupled to detector circuitry, located within the detector unit, or another unit. The detector circuitry filters and amplifies the detector signal and performs signal processing to produce output signals representative of either or both of the in-phase and quadrature components or the phase and amplitude components of the detector signal representative of the magnetic field proximal each detector coil which results from the exciter field generated, relative to the exciter signal driving the exciter coil. The output signals, which are representative of the differences between the phase and relative amplitude of the exciter signal and the detector signal are a function of, inter alia, the pipe wall thickness proximal each coil. The output signals can be encoded into output digital data representative of the output signal in a form suitable for transmission or storage.

In an embodiment selected to transmit the data, the detector unit is preferably connected, by flexible connector means to a unit containing line driver circuitry which conditions and amplifies the output data for transmission through an electric wireline, or other mode of transmission, to the surface for storage or real time analysis. Line driver circuitry is not required for shorter test runs, as is known. Where real time analysis is used, problem areas can be identified during the inspection and the inspection repeated and/or interpretive algorithms used to further characterize the defect. Interpretive algorithms for defect characterization are obtained by correlation of data resulting from test pipes having known defects. Correlation of data with distance information allows defects to be precisely located along the pipe. Non-transmitting embodiments require at least one memory unit, in place of the line driver unit, which houses a memory module for storage of the output data together with data corresponding to timing or distance information. Correlation of timed data and distance information recorded at the surface allows defects to be precisely located along the length of the pipe. Using the non-transmitting embodiment, the stored data is analysed after the inspection of the pipeline by interpretive algorithms. Preferably, the non-transmitting device includes three additional units including, a battery unit, a memory unit and a timer or distance encoder unit.

Leading and trailing anchor units can be attached at the ends of the device for attachment to wirelines or pulling lines. The anchor units preferably contain no circuitry and act to provide attachment to the wireline or the pulling lines to prevent damage to the adjacent units when the device is pulled back along the pipe. The anchor units are preferably shaped to move easily through bends and to prevent them from snagging.

While the housing units of the preferred embodiment have been described and separated according to their function it is to be understood that the device need only carry the circuitry necessary to directly inspect the pipe by RFEC and transmit the signal to the surface. While we have described the device as containing between 3 to 7 units, the number of units can vary depending the use of empty leading and trailing units and on the distribution of the circuitry throughout the units with the minimum number of units being one. This, however, would require the length of the unit to be at least 2× the diameter of the pipe when a sinusoidally varying electromagnetic field is used and would prevent the device from negotiating bends in the pipe. Thus, the reasonable minimum number of units is two. In the preferred embodiment, the units are provided to effectively distribute the circuitry to ensure the size of each unit is suitable to easily move through water distribution pipelines.

BRIEF DESCRIPTION OF THE DRAWINGS

For a better understanding of the present invention, reference may be made by way of ex(ample to the following diagrammatic drawings, in which.

DESCRIPTION OF THE PREFERRED EMBODIMENT

Figure 1:
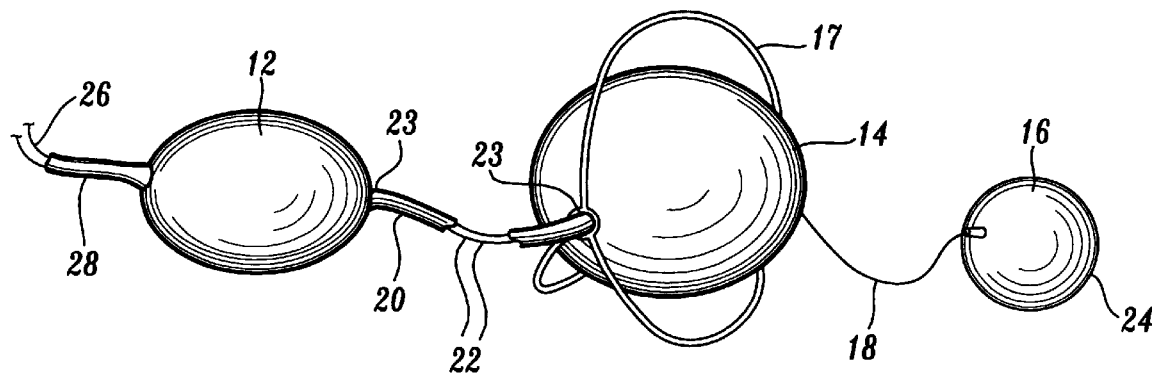
FIG. 1 is a perspective view of an inspection device of the present invention.

Referring to FIG. 1, a device 10 for inspecting the integrity of a pipe comprises a plurality of housing units 12, 14, 16 which are sized to fit within, and move freely along, the bore of the pipe. Each unit 12, 14, 16 is rounded on its leading and trailing ends to prevent snagging on discontinuities within the bore. The units house inspection devices and electrical circuitry and, thus, are sealed against entry of fluids.

Where a unit of the inspection device requires axial alignment within the pipe, such as unit 14, centralizers 17 can be mounted on the unit.

The units 12, 14, 16 are connected by flexible connectors such as cable 18 or flexible tubing 20 to allow device 10 to flex around bends. Flexible tubing 20 permits communication between the units and has been cut away to show use as a conduit for electrical wires 22 which extend between units 12, 14. Tube 20 is sealed at its connections 23 to units 12, 14 by tapered thread and Teflon tape to prevent entry of fluid.

Device 10 is moved along the pipeline by connection, via pulling line 24, to a moving means such as a pulling pig (not shown), where fluid flow is maintained in or applied to the pipeline, or a collector such as a winch or other device (not shown).

Surface communication can be provided by wireline 26 which can be sheathed in a flexible tube 28 or its own armour.

Pulling line 24 or wireline 26 can be marked to indicate the length of line to device 10 and thereby provide an indication, from the surface, of the device location along the pipe.

Device 10 can be used in various ways to inspect pipe condition. Preferably, the inspection is initiated through an access point such as a hot tap, a hydrant or a hydrant adapter. Inspection through hydrants is preferred since excavation is avoided. The device can be used to inspect operating pipeline. Preferably, however, the section of pipeline to be inspected, including any required access hydrants, is isolated and depressurized. The device is preferably moved along the pipeline by pulling or by applied water pressure acting on a pulling pig. After the section has been inspected, the device can be removed by pulling back along the same path or by use of an exit point such as a hydrant.

The device of the present invention allows access to pipeline via tees and Y-shaped insertion paths, such as through hydrants, because of the flexibility of the device and compactness of the circuitry housing units.

Figure 2A:
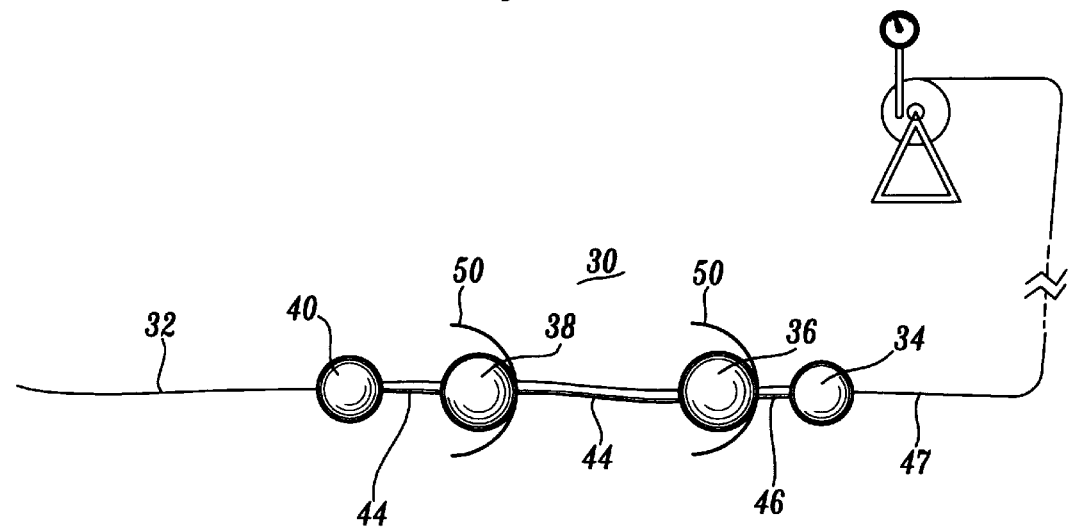
FIG. 2A is a mechanical schematic view of a transmitting embodiment of the RFEC inspection device of the present invention.
Figure 2B:
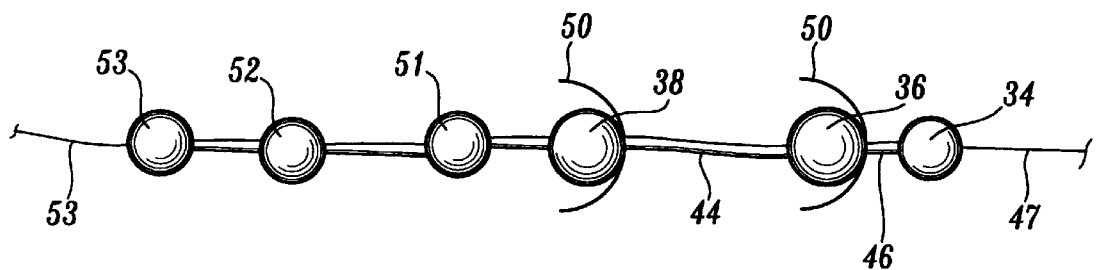
FIG. 2B is a mechanical schematic view of a non-transmitting embodiment of the RFEC inspection device of the present invention.

Referring to FIGS. 2A and 2B, an inspection device using RFEC technology may be made according to the present invention.

A first embodiment of an RFEC device 30 having electrical contact with the surface is shown in FIG. 2A. This embodiment includes an electric wireline 32 which connects to the device, either at the leading end or the trailing end, as shown. Where required, wireline 32 should be of sufficient strength to provide a means for pulling the device along the pipeline.

The wireline can provide for one or both of data transmission and power supply. The wireline armour, where it is made of conductive material such as carbon steel, can be used as the ground reference. The data is transmitted along the wireline in digital form which is preferably coded for transmission, using for example, Manchester coding and decoding or any other suitable data coding and conversion means. The surface data reception circuitry interfaces with a personal computer and performs functions to convert the data back into the in-phase and quadrature components or the phase and amplitude components of the output signal produced by the detector unit 38. Presentation software displays the data on a computer output. Output can be in the form of four traces representing amplitude, phase, real and imaginary components all plotted versus distance along the pipeline. Sharp changes or deflections in the traces along the pipeline are identifiable as anomalies that are considered to be defects on the interior or exterior surfaces of the pipe wall.

In one embodiment, device 30 comprises five housing units including: a leading anchor unit 34 for mechanical connection to the pulling pig or cable; an exciter unit 36 housing an exciter coil and related circuitry; a detector unit 38 housing at least one detector coil and related circuitry; and, a line driver unit 40 housing circuitry for conditioning and amplifying the data for transmission to the surface.

Flexible connectors 44 space the exciter unit 36 from the detector unit 38 and preferably include a tubular member to carry electrical wires for communication between the units. Any connections which do not provide for communication between the units, such as connection 46, can be accomplished by means of a cable.

The leading unit 34 is pulled by means of a pulling line 47 by attachment to a pulling pig or a surface pulling means, such as a winch 48. Preferably, winch 48 is fitted with an odometer 49 which records the distance information relating to the movement of the device through the pipeline and which data can be correlated to the defect information. Where desired, a winch, with or without an odometer, can be provided for attachment to wireline 32.

Units 36 and 38 are maintained in axial alignment with the bore of the pipe by means of centralizers 50. Units 36 and 38 are preferably separated by a distance of at least 2× the pipe bore diameter.

An embodiment which does not transmit and, thus, does not require an electrical wireline is shown in FIG. 2B. In this embodiment, leading unit 34, exciter unit 36 and detector unit 38 remain as in the embodiment of FIG. 2A. In the preferred non-transmitting embodiment, a unit 51 is connected to detector unit 38 which houses a memory module for storing the data and a module for compressing the data. Preferably, a unit 52 housing device locating means such as a timer and/or an odometer means (ie. a wheel disposed to ride against the internal pipe wall connected to an optical encoder, for example, that known as Express™ Encoder model H25 available from BEI Sensors & Systems Company), and a unit 53 housing the battery pack are also included in the non-transmitting device. To shorten the length of the device, the circuitry of units 51, 52 and 53 can be redistributed to remove some of these housing units.

The non-transmitting device includes a trailing line 54 to allow the device to be pulled back along the pipe or to be held back against the action of the water pressure. The devices of FIGS. 2A and 2B can have measurement markings on their pulling lines 47, trailing line 54 or wireline 32 to permit the location of the device along the pipeline to be determined.

The device of the preferred embodiment uses both analog and digital technology to provide high resolution RFEC analysis. The circuitry design is modular, both to fit within the housing units and to alleviate problems with crosstalk, which tends to interfere with the measurement of the $\mu V$ level signals in the detector circuitry, and other interactions observed in earlier design approaches. The modular design of the circuitry also facilitates expansion to accommodate various numbers of detectors. For example, systems including six channels can be expanded to accommodate twelve channels simply by adding an additional detector circuitry module.

Power for the modules is provided by DC—DC converters operating from a DC supply voltage provided via the wireline or by batteries within the device.

Figure 3:
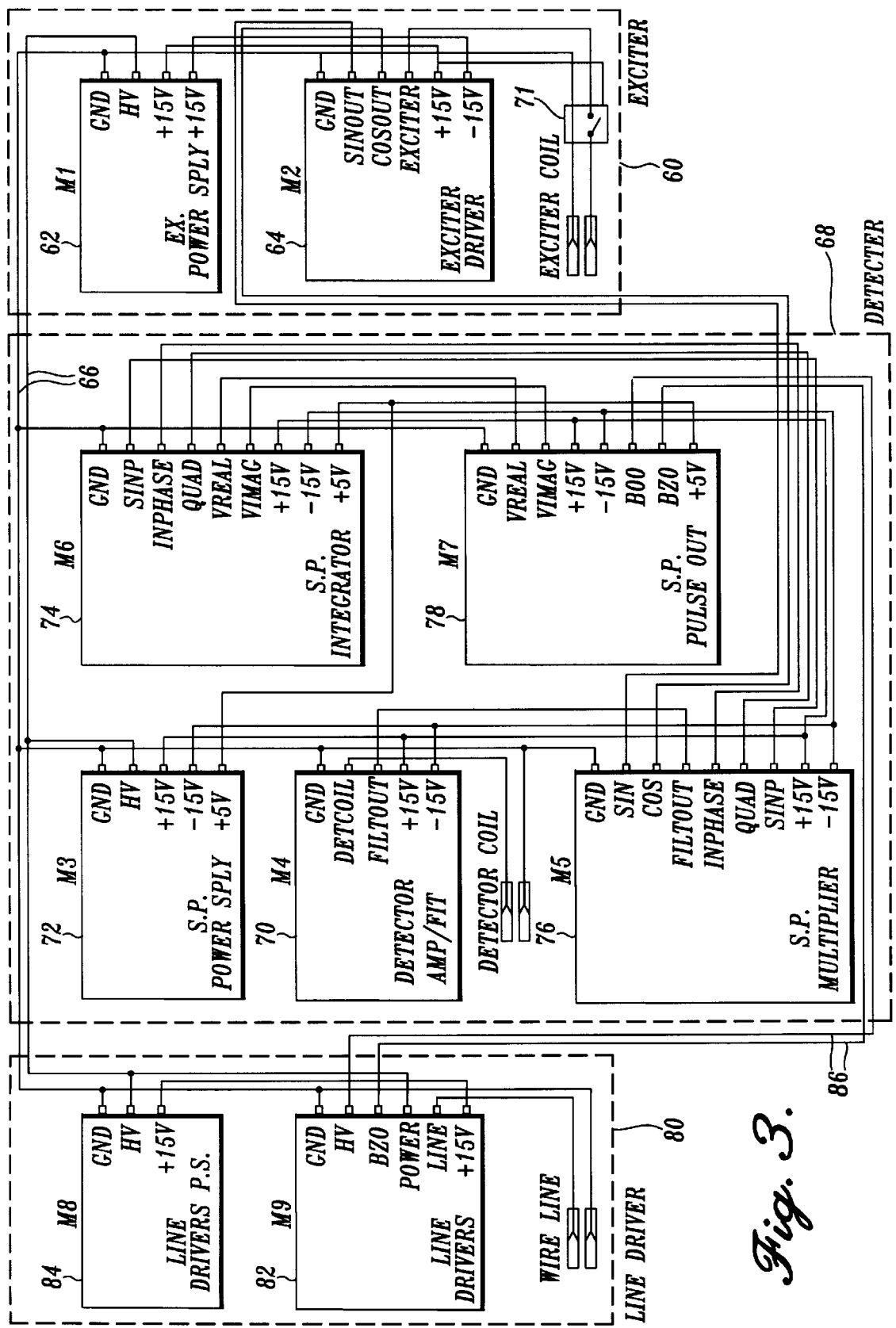
FIG. 3 is a functional block diagram of the electrical components of one embodiment of an RFEC inspection device.

FIG. 3 shows a functional block diagram illustrating the electrical components and interconnection of the exciter unit, detector unit and line driver unit useful for a transmitting embodiment as shown in FIG. 2A.

The exciter unit circuitry 60 comprises an exciter coil power supply 62 and a exciter coil driver 64. Driver 64 provides outputs of the in-phase and quadrature signals corresponding to the exciter signal for use by the detector unit 68. Exciter coil driver 64 produces the exciter signal for energizing the exciter coil. Power is supplied via lines 66 which are connected to the wireline. Alternately, power can be supplied from a battery (not shown) or generator means for self-supply of energy to operate the device.

The detector unit circuitry 68 comprises a detector amplifier and filter board 70 which receives the microvolt output of the detector coil. Circuitry 68 amplifies the signal received from the detector coils to a level suitable for signal processing and performs suitable filtering, such as low-pass filtering to remove or reduce the noise content of the signal. A signal processing system is provided comprising a power supply 72, integrator 74, multiplier 76 and pulse output 78. The signal processing system produces an output signal based on input detector signal and exciter signal. The output signal can be representative of one or more components or characteristics, including the phase difference between the exciter signal and the detector signal, the relative amplitudes of the two signals, or the in-phase and quadrature components of the two signals. More involved time-frequency domain transformations can be employed to provide other useful output signals. For each component, the output signal can be a voltage level or, preferably, further processed into digital data stream suitable for data transmission or storage. Preferably, the in-phase and quadrature components of the signal are converted to their 12 bit binary representation. The binary data is sent to the line driver circuitry which does the Manchester encoding. The line driver circuitry includes a wireline driver and a power supply. The circuitry acts to convert the binary data into encoded binary data with sufficient output to drive the low impedance of the wireline.

The line driver unit circuitry 80 comprises a wireline driver 82 and a power supply 84. Circuitry 80 acts to convert the output signal, which are preferably pulse trains received via lines 86 from the pulse output 78 of the signal processor system into pulse trains with sufficient output capability to drive the low impedance of the wireline sufficient to reliably detect the output signal at the other end of the wireline remote from the device 10.

Because the exciter coil draws a large current during start up, it is preferable to provide a power-up isolator 71 which isolates or disconnects the exciter coil from the exciter driver 64 for a pre-determined time-delay, extending for several milliseconds, to minimize current drain during power-on startup. This isolator properly sequences the start up to avoid a large voltage drop over the wireline. This permits the remainder of the electronics to start up before power is applied to the exciter coil.

FIG. 3 illustrates a functional block diagram of an electrical arrangement useful in the present invention. It is to be understood, however, that the circuits can be distributed throughout the tool in other ways, as desired. For example, in one embodiment, the signal processing circuitry is separated from the exciter and detector circuitry to provide a more modular design. The exciter circuitry can generate the in-phase and quadrature components for signal processing.

Figure 4A:
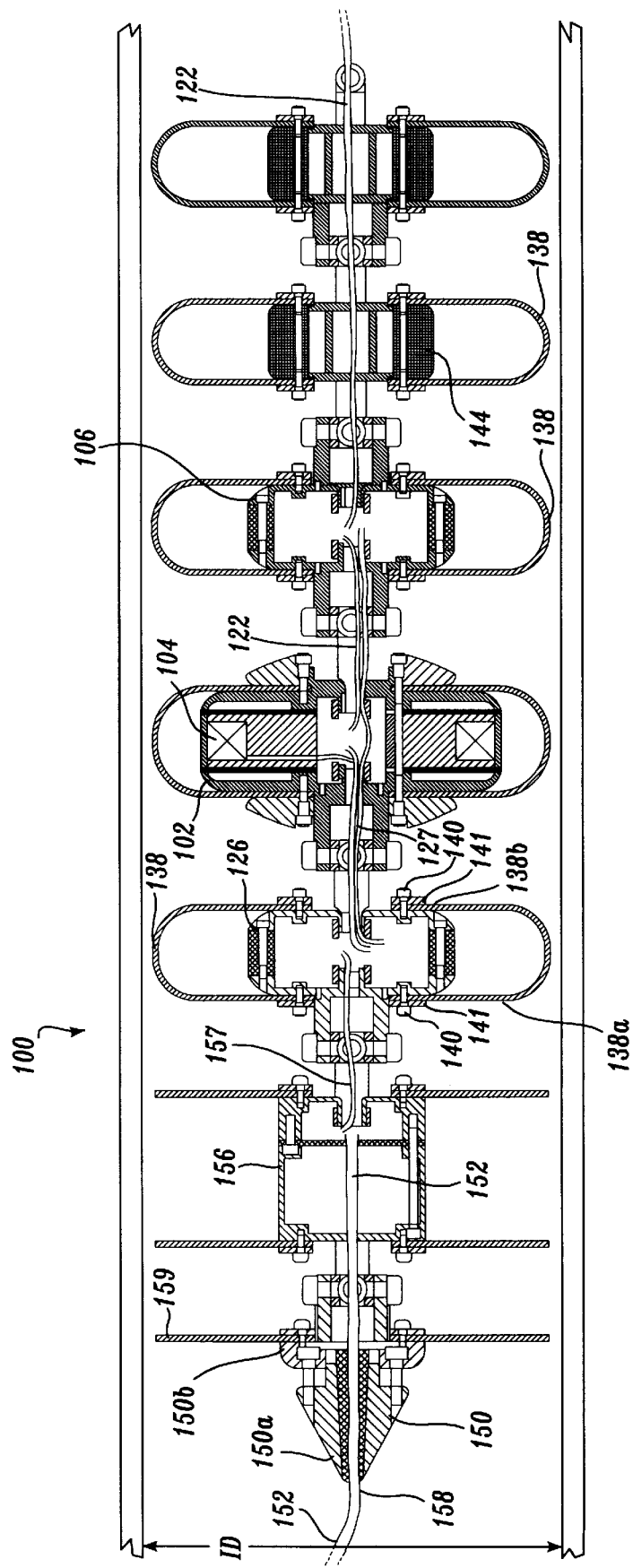
FIG. 4 is a sectional view through an RFEC inspection device.
Figure 4B:
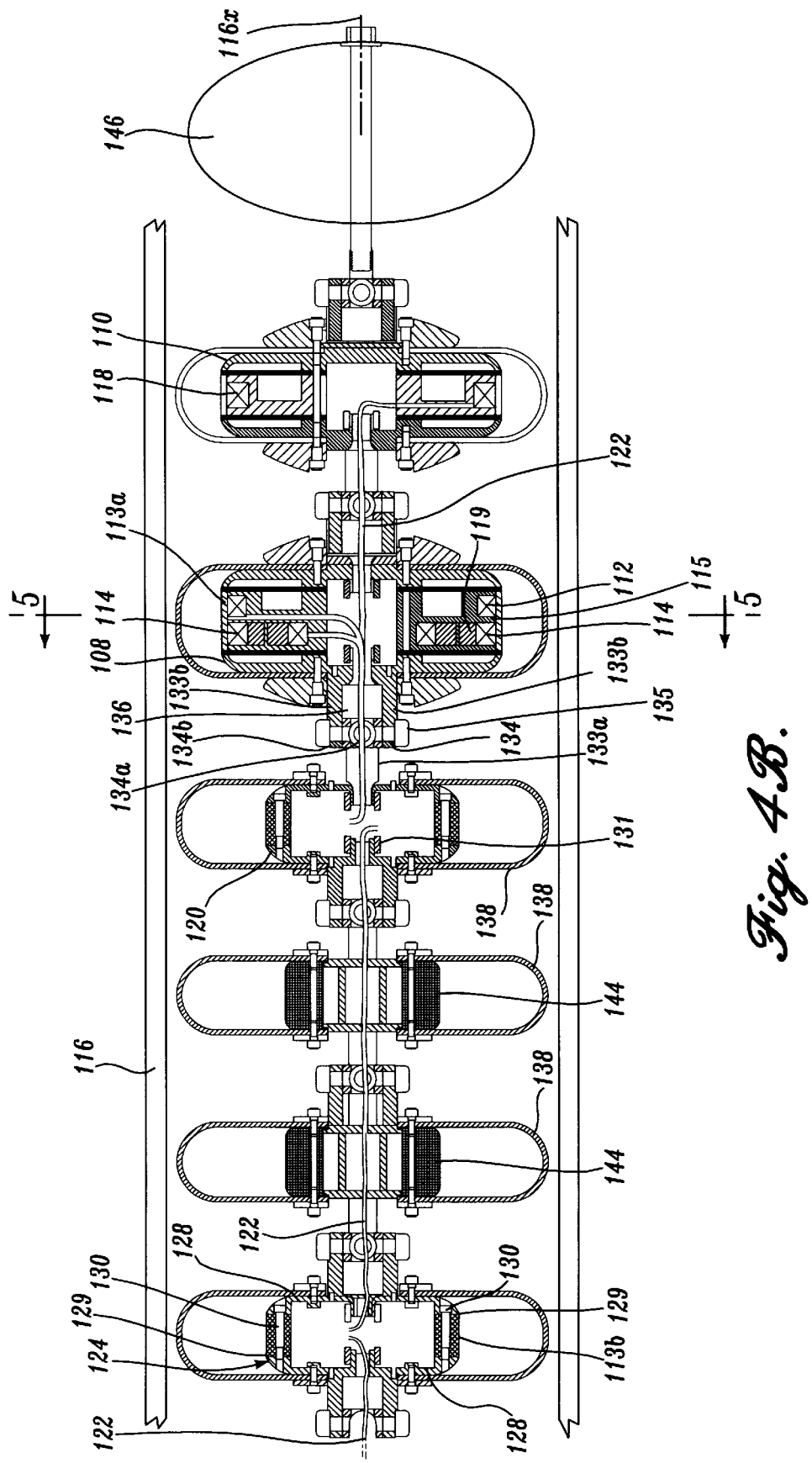
Figure 5:
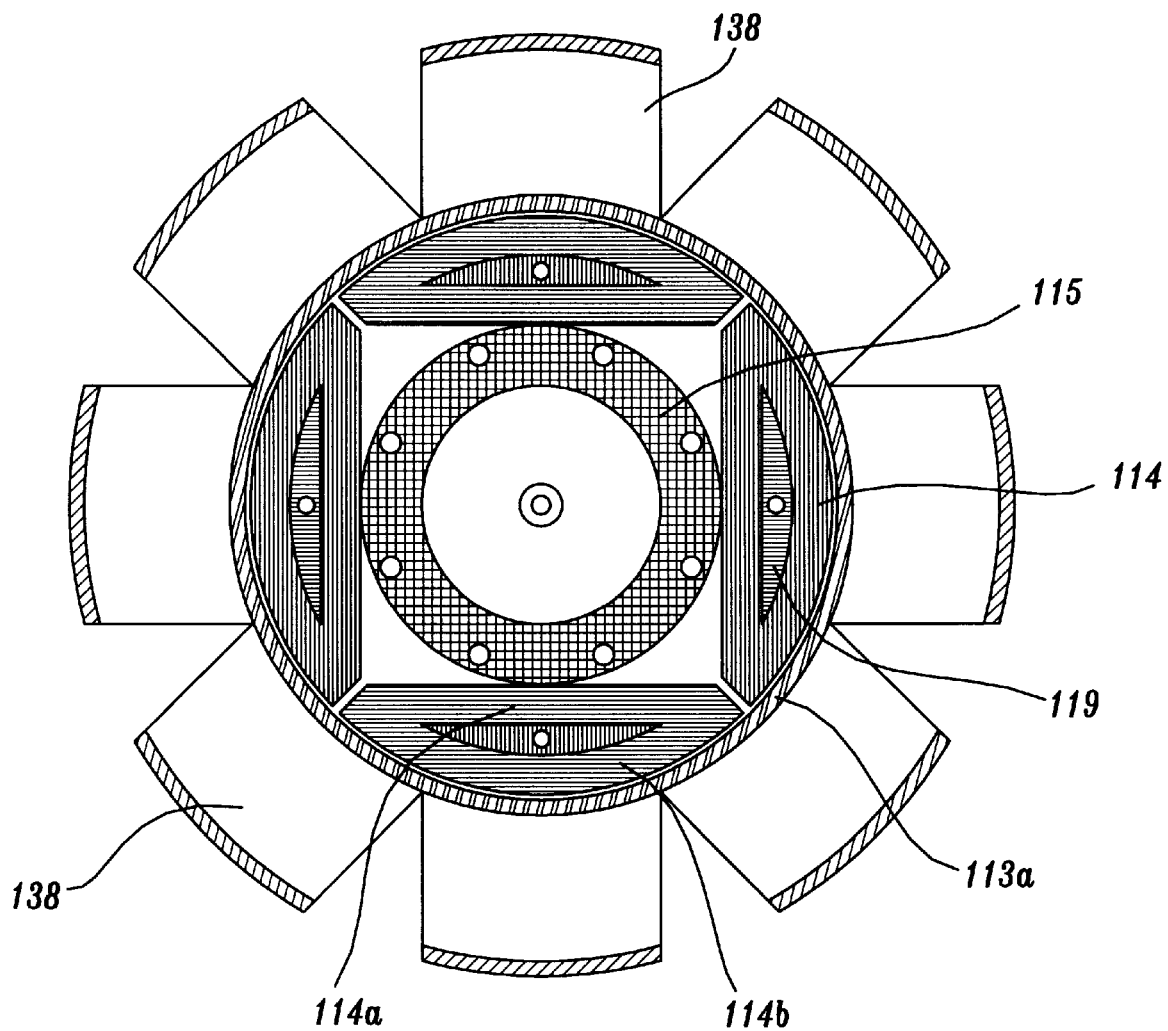
FIG. 5 is a sectional view along line 5—5 of FIG. 4.

Referring to FIGS. 4 and 5, the mechanical features of the embodiment of a pipe inspection device 100 in accordance with the invention are shown. Device 100 houses RFEC inspection circuitry. Device 100 includes a unit 102 housing a full circumferential, axial exciter coil 104 and, because space within the unit is limited, another unit 106 housing the exciter circuitry (not shown).

A group of detector coils is housed in two units 108, 110. While various groups of detector coils are useful, the first unit 108 houses an axial coil 112 with a diameter slightly smaller than the that of outer circumferential wall 113a of the unit and a plurality of spot coils 114 spaced apart adjacent the outer circumferential wall 113a of the unit. The second unit 110 houses a full circumferential, axial coil 118 similar to coil 112. The coils are accommodated in cavities formed in the bodies 115 of their respective units. The circuitry for the detector coils 112, 114, 118 (as described with reference to FIG. 3) is housed in an adjacent unit 120.

The spot coils 114 are each positioned substantially at the same position along the axis 116x of the device. Each spot coil is arranged to detect the axial component of the magnetic field with its axis being substantially parallel with the axis 116x of the pipeline 116 which is to be inspected. While four spot coils are shown mounted in the device, any desired number of spot coils can be used therein. For example, in a device for inspection of 6" ID pipes, six or eight spot coils can be spaced apart evenly about the outer wall; twelve coils are preferred in a device for 12" ID pipes; and 20–25 coils are preferred for a device for 20" ID pipes.

Spot coils 114 are preferably D-shaped, being wound around a spool 119 to have a flat side 114a and a curved side 114b. The coils are positioned in a ring with their curved side adjacent circumferential wall 113a of the unit. Preferably, side 114b has a curvature which conforms to the curvature of the circumferential wall. The shape of the coils and their end to end positioning permits the entire circumference of the device to be accommodated by windings. The use of D-shaped coils improves the sensitivity of the device to small anomalies.

Detector coils 112 and 118 are spaced apart a known distance. When these detectors register a defect, the responses for the coils will be recorded as being this known distance apart. However, when the exciter registers a defect, the response will be recorded simultaneously on both detector coils 112 and 118. Thus, this arrangement of axial detectors of similar architecture permits exciter responses to be distinguished from detector responses. In addition, the coils 112 and 118, although preferably operated in the absolute mode, can be used as differential coils by signal vector subtraction using computer data manipulation. Alternately, coils 112 and 118 can be connected in the differential mode. As is known, where a differential signal is being determined between two coils, preferably those coils are selected to have similar geometries, for example in terms of number of windings, diameter, etc. This is especially preferred where the coils are positioned close together.

Exciter coil 104 is spaced from the detector at a distance sufficient to produce remote field eddy current interaction in the pipe wall extending between the coils. In the embodiment shown, the exciter coil generates a sinusoidally varying field and a spacing between the detector and the exciter of at least two pipe internal diameters (ID) from the closest detector coil 114 is preferred. Electrical communication is provided by electrical conductors 122 (shown schematically) extending between exciter coil 104, and its related circuitry in exciter unit 106, and detector coils 112, 114 and 118 and their related circuitry housed in unit 120. Between the exciter units 102, 104 and the detector units 108, 110, 120 is a digital signal processing unit 124 housing circuitry which controls the functioning of the exciter and detector circuitry, filters the data and calculates the in-phase and quadrature components. Unit 124 can be located at any position along the device. Conveniently, unit 124 can be positioned in the space between the exciter and detector units to reduce the length of the device. However, preferably unit 124 is distanced from high power units such as the exciter unit 102 a sufficient distance to avoid interference with the electronics of unit 124. Because the power supply for the digital signal processing unit 124 may be produce electrical noise, it is also preferred that unit 124 be spaced from the detector electronics unit 120 a sufficient distance such that the noise produced does not interfere with the microvolt detector signals supplied to the detector electronics by the detector coils.

The device also includes a transceiver unit 126 which houses transceiver circuitry for sending and receiving signals through the wireline, Manchester encoder and line driver circuitry, if desired. The circuitry in transceiver unit 126 is connected to the circuitry in exciter circuitry unit 106 by electrical conductors 127 (shown schematically in FIG. 4).

The units containing circuitry or coils are sealed against the entry of water. Referring for example to unit 124, each unit preferably includes side plates 128 and a circumferential wall 113b formed of thermoplastic or stainless steel. Gaskets 129, or other sealing means, are provided between the wall 113b and the side plates 128 and the unit is held together by fasteners 130 such as screws.

Electrical conductors 122, 127 extend between the units. Ports, for example port 131 on unit 120, through which conductors 122, 127 extend are sealed to prevent entry of water into the units. The conductors 122, 127 themselves can be coated with water blocking insulation and can extend separately between the units, as shown. Alternately, a protective sheath can be secured about groups of conductors or a flexible conduit can be provided between adjacent units through which the conductors can extend. Each unit of the device is connected to its adjacent unit(s) by a flexible connector formed by two pairs of shafts 133a, 133b (only one shaft 133a can be seen in FIG. 4). Each shaft 133a, 133b supports at its end a bushing 134a, 134b. Shafts are joined by a gimbal-type universal joint assembly 135. The universal joint assembly provides for flexing of the connection between the units as joint 135 can independently pivot in bushings 134a and in bushings 134b. Between each pair of shafts is defined a protected inner cavity 136 through which electrical conductors 122 can pass.

Each unit has secured thereto a plurality of centralizers 138. Preferably, the centralizers are formed from polymeric material, for example polyurethane, and are formed as loops having a first end 138a secured against one side plate 128 and a second end 138b secured against the other side plate. Other centralizers can be used for example polyurethane annular flanges having slits extending radially therein, brushes, and spring biased arms. However, centralizers formed of polymeric material and particularly those formed as polymeric loops reduce the travel noise generated by movement of the device through a pipeline and can facilitate inspection data collection.

The loops are secured to the side plates by any suitable means such as fasteners 140 and clamping rings 141. The loops can be reinforced to reduce abrasive wear thereto by use of ceramic filled polymers or by coating with a Kevlar-based material such as Kevlar textile.

To facilitate the passing of bends, preferably centralizers are positioned at regular intervals along the device. Spacer units 144 having centralizers 138 mounted thereon are spaced between the exciter units and the detector units. Spacer units 144 can be formed in any convenient way and of any suitable material. Preferably, the spacer units are formed of light weight materials such as the thermoplastic Nylatron. To reduce weight and reduce the effect of water pressure on the device, the spacer units are preferably formed as rings with open central apertures through which water can pass.

A pulling pig 146 is attached at a first end of the device. Pig 146 is shaped to be acted upon by fluid pressure to move the device along a pipeline. Pig 146 is connected to the device by a flexible connector in the form of a shaft having a pivotally moveable joint, generally as described hereinbefore. Preferably, the pulling pig is formed of a durable material such as polyurethane foam. Where it is not desired to use fluid pressure to move the device along a pipeline, pulling pig 146 can be replaced by a line anchor unit similar to wireline anchor unit 150 shown connected at the opposite end of the device. Attachment of a line anchor unit permits the device to be pulled through a pipeline by a winch or other moving means located at the access point to the pipeline.

A wireline 152 is connected to the device by means of the wireline anchor unit 150 and passes into a splice ball 156 where the conductors of the wireline are spliced to conductors 157 which communicate with the circuitry of the transceiver and therethrough to the inspection circuits. Wireline 152 carries conductors for power and data transmission. The wireline is formed to be sealed against the entry of water into its core housing the conductors. An outer layer or layers of steel wire strengthen the wireline and prevent damage thereto. Wireline 152 can withstand some pulling stress as it is dragged behind the device which is being propelled by water pressure acting on pulling pig 146. However, the wireline can withstand only limited pull loads. To hold the device back against strong water pressure, a dedicated wire rope of high break resistance is required. Such a wire rope will generally not include any electrical or data conductors. In such an arrangement, the wireline can be placed to extend in front of the pulling pig and a two winch system can be used to control the supply of wireline and wire rope. In this arrangement, the pulling pig is formed to anchor securely the wireline and the splice ball is moved adjacent the pulling pig and the anchor unit at the end opposite the pulling pig can be used to secure a trailing line such as a steel cable which is used to hold the device back against the water pressure.

To facilitate passage of anchor unit 150 around corners, preferably the unit is formed to have a tapered leading edge 150a. Additionally, the anchor is formed such that the point 158 through which wireline 152 enters the anchor unit 150 is substantially held away from the pipeline wall. Thus, centralizers 159 are mounted at the trailing edge 150b of the anchor unit 150.

The device of FIG. 4 includes a digital signal processor, exciter drive electronics, amplification and filtering electronics and transceiver electronics. Preferably, the digital signal processor includes a sine generator means, a band-pass filter means and means for multiplication and integration. A useful digital signal processor is available from Texas Instruments Inc. The sine generator means generates the sine wave for the exciter drive circuitry as well as the reference sine wave for the detector analysis algorithm of the digital signal processor. The digital values of the sine wave sent to the exciter drive electronics are updated 128× per period. The values for the reference sine are updated 16× per period. The reference values are used by the multiplication algorithm, as will be discussed hereinafter, of the digital signal processor which performs a 16 bit multiplication between the filtered digital data from the detector coils and the reference values. The band-pass filter of the digital signal processor reduces power line noise of the detector signals coming from the detector coils. Preferably, the digital signal processor algorithm is implemented using a 100-tap FIR band-pass filter, which provides 58-dB rejection at 60 and 120 Hz for an 85 Hz exciter frequency. The digital signal processor code for the multiplication algorithm performs a multiplication 16× per exciter period. The result is stored in a 16 bit word. Integration is performed used a trapezoidal integrator algorithm. The integration is done over one exciter period. The integration yields the output of the digital signal processor unit and this output is sent to the transceiver ball through serial communication.

The exciter drive electronics converts the digital sine wave values from the digital signal processor into a real sine wave using a digital-to-analog converter. A useful converter is, for example, a MAX532BCWE chip available from Maximum Integrated Products Inc. The conversion is carried out 128× per exciter period. The output of the digital-to-analog converter is then fed to the power amplifiers, which drive the exciter coil. The exciter coil amplification circuitry is built around two operational amplifiers. Suitable amplifiers are, for example, those in the APEX PA21 package available from Apax Microtechnology Corporation. During start-up of the device, the amplifiers are maintained off until a relay, for example a relay such as a TQ2E-12V relay available from Aromat Corporation, in the exciter drive electronics is activated. By maintaining the amplifiers off no current is sent to the exciter coil. This start-up delay circuitry limits the initial start-up current.

The amplification and filtering electronics includes a programmable gain amplifier (PGA), a first order passive filter, a switched capacitor filter, a multiplexer and a level shifter. The first stage of the detector signal conditioning circuitry includes the PGA. The gain of the PGA can be set to any multiplication, for example 1×, 10×, 100× or 1000×. The PGA circuitry can be, for example, built around the PGA204 chip available from Burr-Brown Corporation. The output of the PGA is filtered using a first order passive filter such as a low pass filter consisting of a capacitor and a resistor. This filter functions to reduce high frequency noise. After the first order filter, the detector signal is heavily filtered using an 8th order switched capacitor filter. The filter can be built, for example, using a MAX296 chip, available from Maxim Integrated Products Inc. This filter functions as both an anti-aliasing and a noise removal filter. The next stage in the amplification and filtering electronics is the multiplexor, which allows the operator to bypass the low pass filters, if required. The multiplexor can be omitted but is useful for troubleshooting. The last stage of the amplification and filtering electronics circuitry is the level shifter. The level shifter shifts the signal level of the multiplexor output to the proper input range for an analog-to-digital convertor. The level shifter circuitry can be, for example, built around a OP491GS chip available from Analog Devices Inc. The analog-to-digital convertors which can be, for example, LM12438 chips available from National Semiconductor Corporation, are read out by the digital signal processor. Each detector coil has its own amplification, filtering and level shifter circuitry.

The front end amplification and filtering circuitry together with the digital signal processor form a lock-in amplifier that has been optimized for fast response and for operation at low frequencies, for example 20 to 300 Hz. A suitable lock-in amplifier is, for example, model 5205 amplifier of EG&G Inc.

The transceiver electronics read in the command signals from a computer, for example located on ground surface, and send information back from the digital signal processor. The signals from the computer are differential +/−10V signals, which the transceiver converts to standard transistor-transistor logic (TTL) level signals. The chip responsible for the conversion to TTL can be, for example, the DS8935 chip available from National Semiconductor Corporation. The TTL signals, which are Manchester encoded for passage through the wire line, are decoded. A useful chip for Manchester decoding is the HD6409 chip available from Harris Corporation. The decoded signals are then checked for errors by evaluating a checksum. If the checksum does not correspond with the data packet, the transceiver will send a request for a retransmission to the ground surface computer. Checksum evaluation can be done for example by use of a Microchip Technology Inc. chip no. PIC16C73.

Data to be sent from the digital signal processor through the wire line to the ground surface computer is first provided with a checksum. This can also be done using a PIC16C73. Next the data is Manchester encoded preferably using the same chip that does the Manchester decoding. Finally, the encoded binary data is sent to the DS8935 chip, which drives the data over the wire line using a differential +/−10V signal. All chips in the transceiver electronics can perform both the send and receive functions. Therefore, only one of each chip is required in the device.

Figure 6:
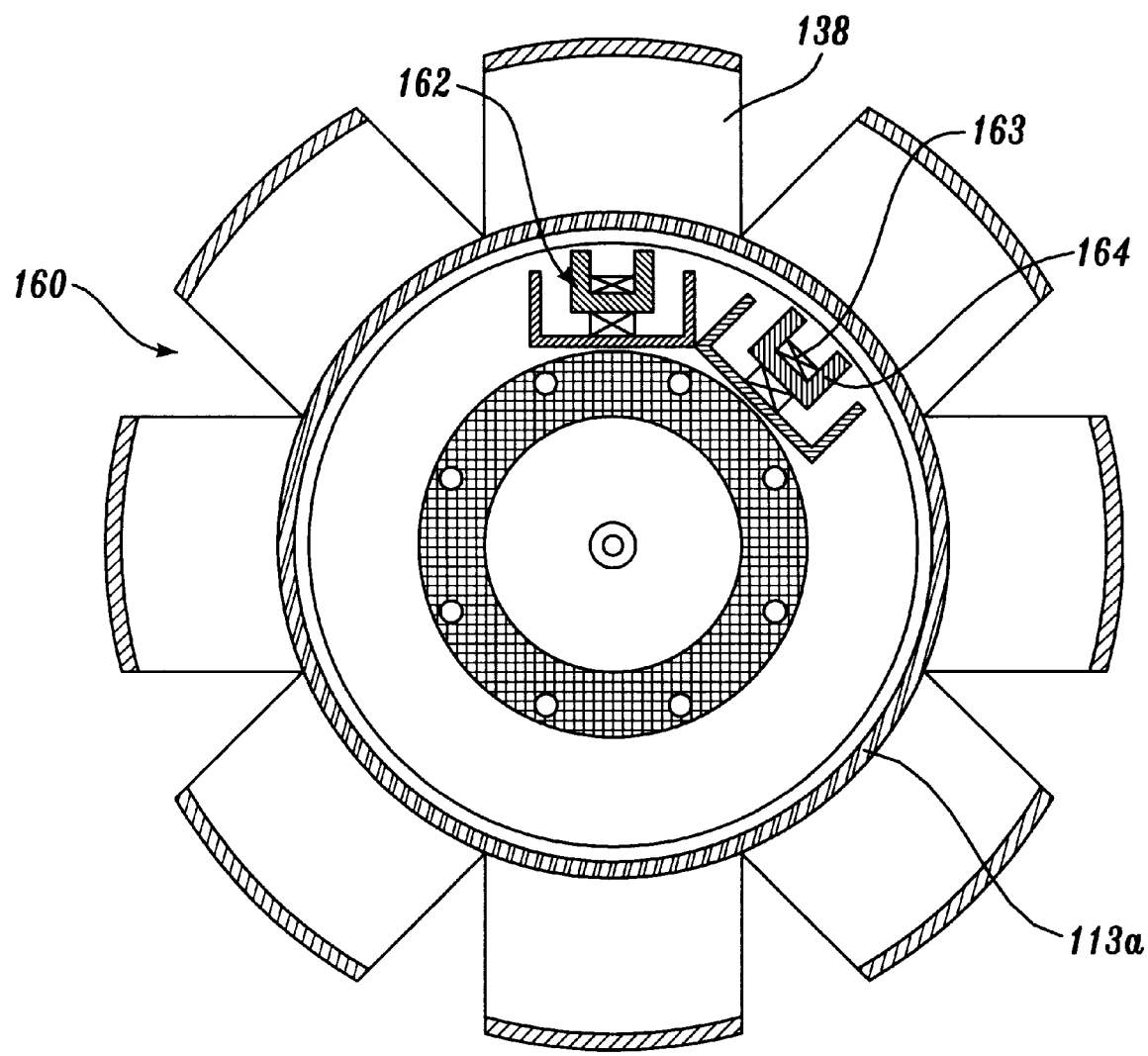
FIG. 6 is a sectional view through another detector unit useful in the present invention.

FIG. 6 shows a sectional view through a detector unit 160 having another detector coil arrangement according to the present invention. The unit includes a plurality of spot coils 162 spaced apart adjacent outer circumferential wall 113a. While only two coils are shown in order to simplify the drawing, any number of coils can be used in a detect on unit. Each spot coil 162 has windings 163 around a U-shaped core 164. Such a detector coil arrangement increases the sensitivity of the device to field perturbations caused by defects over detectors not having coils with U-shaped cores. Each coil 162 has disposed thereabout a shielding cup 166 formed of metal which acts to remove a portion of the background field.

Figure 7:
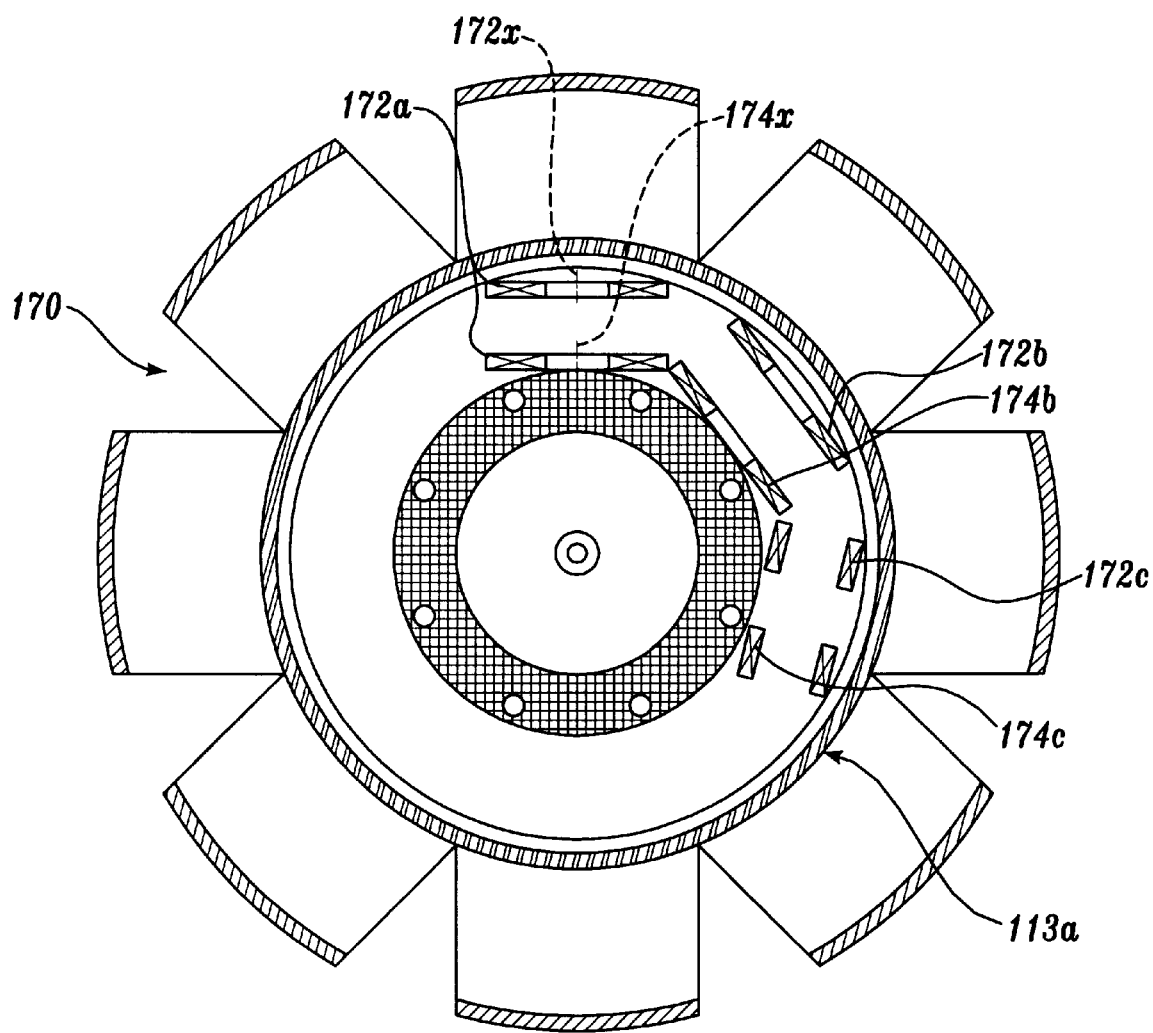
FIG. 7 is a sectional view through another detector unit useful in the present invention.

Another detector coil arrangement according to the present invention is shown in FIG. 7. A detector unit 170 houses an outer ring of spot coils 172a, 172b, 172c disposed to measure the radial magnetic field and an inner ring of spot coils 174a, 174b, 174c disposed to measure the radial field (only three coils from each ring are shown in order to simplify the drawing). The rings of coils 172a–c, 174a–c are positioned at substantially the same position along the axis of the tool. The ring of coils 172a–c is disposed between outer circumferential wall 113a and the ring of coils 174a–c. The coils are further positioned such that the axis 172x of each coil in the outer ring, for example 172a, is substantially aligned with the axis 174x of one coil, for example 174a, in the inner ring. In this arrangement the coils having their axes aligned can be considered used as a coil pair, for example 172a and 174a, for defect detection. A coil pair can be used to determine a differential signal. The differential signal can be produced by connecting the coils of the coil pair differentially or a differential signal can be calculated from signals detected by each pair of coils (i.e. by subtraction of the signals). Such differential signals provide a reduction in the effect of travel noise over other radial detector coil arrangements.

Figure 8A:
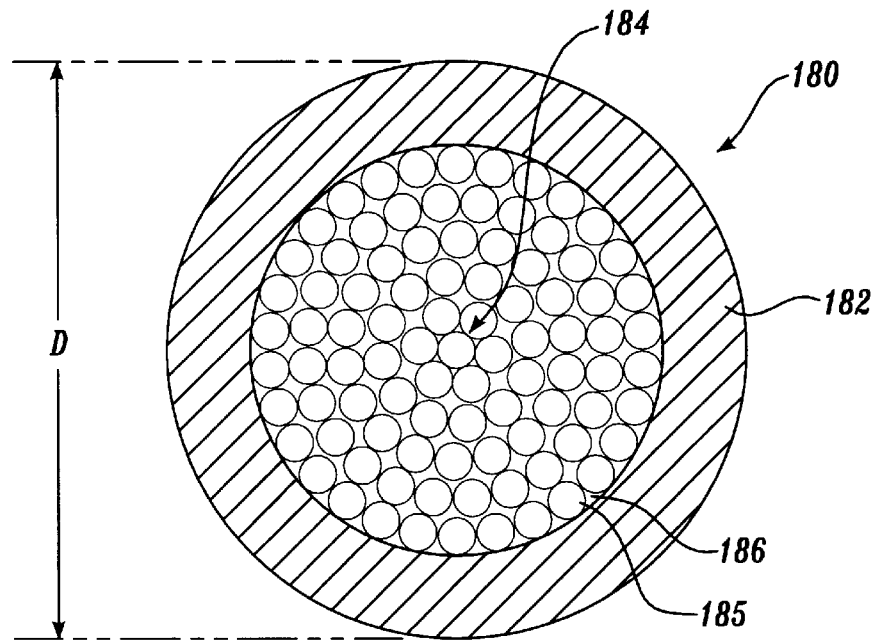
FIG. 8A is a plan view of a coil useful in the present invention.

Referring to FIG. 8A another detector spot coil 180 useful in the present invention is shown. The coil has windings 182 wrapped circumferentially about a circular core 184. Core 184 is formed of an aggregate of high-$\mu$ particles 185 with electrically insulative material 186 disposed therebetween. In one embodiment, the core is formed of a bundle of high-$\mu$ electrically conductive metal wires. The wires extend from one side of the core to the other and have electrically insulative material disposed therebetween to insulate each wire from each other wire in the bundle. Coil 180 is selected such that its diameter D is about the same size or smaller than the smallest defect which is desired to be detected using the coil. Coil 180 will magnify both the noise and signal over a similar coil not having the core as described. Appropriate signal processing such as filtering software or differential connection of two such coils can be used to remove the noise and boost the signal level. A coil, as shown, may introduce non-linearities into the detector signal. However, where the M-H properties of the coil are known, these non-linearities can be removed by data manipulation, as is known.

Figure 8B:
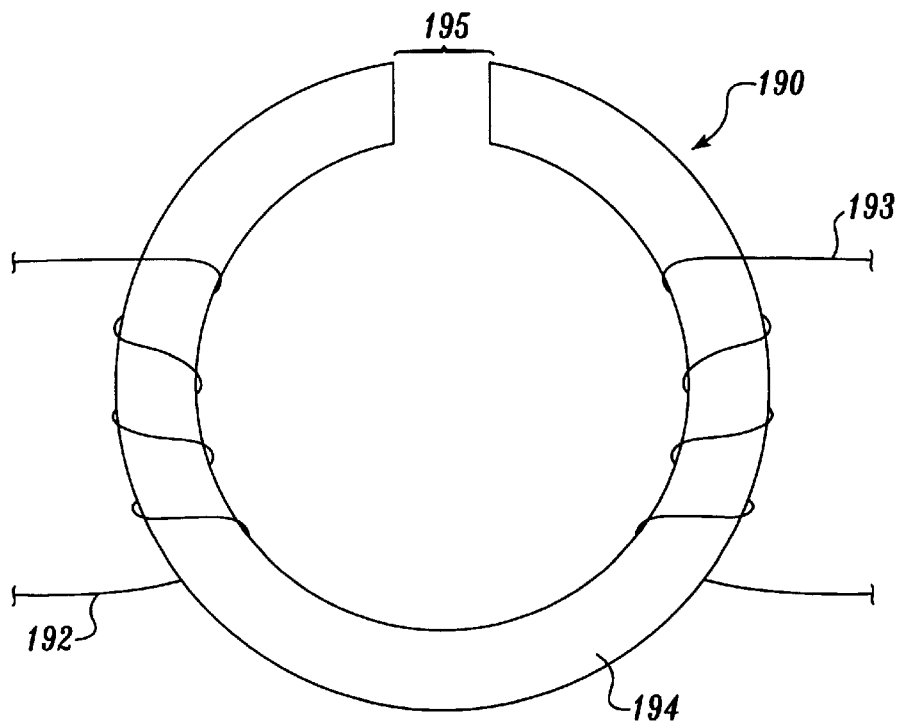
FIG. 8B is a plan view of another coil useful in the present invention.

Another useful detector spot coil 190 is shown in FIG. 8B. Coil 190 has two windings 192, 193 about a C-shaped read-head type core 194. Core 194 is formed of a high-$\mu$ material such as ferrite and has an air gap 195 which is characteristic of read-head type cores. The two windings can be connected in phase or out of phase. The two windings can be replaced with a single winding where desired. The results obtained by use of a coil such as that shown in FIG. 8 are comparable to coils 162 in FIG. 6.

The following specific example is given to further set forth operation of the invention, it being understood that the example is by way of illustration only and is not to be construed as limiting the scope of the invention.

EXAMPLE 1

A device of the present invention and generally as described in FIGS. 2A and 3 was used to inspect a water distribution pipeline located in Northeast Calgary, Alberta, Canada. The line, measuring 200 m, was scheduled for excavation and replacement and had been in service for approximately 18 years.

The line was isolated and depressurized. The device was then fed to the line via a standard McAvity hydrant, with the valve stem removed. Hoses from adjacent hydrants provided Nater pressure which acted on a pulling pig attached ahead of the device to pull the device through the line. A wireline was attached to and trailed behind the device and provided power and data transmission to the device. The wireline was marked to provide distance information.

The device passed through the line and traversed a number of elbows and tees, as well as numerous service connections and at least one repair clamp. The device moved along the line without snagging and exited at an exit port.

Wall discontinuities along the line were located by correlating collected data with distance information gained by recording advancement of the wireline along the line.

It will be apparent that many other changes may be made to the illustrative embodiments, while falling within the scope of the invention and it is intended that all such changes by covered by the claims appended hereto.

The embodiments of the invention in which an exclusive property or privilege is claimed is defined as follows:

1. A remote field eddy current inspection device for water pipelines comprising:

(a) an exciter unit housing an exciter means for producing a time-varying magnetic field in response to an exciting signal;

(b) a detector unit housing at least one detector means for producing a detecting signal representative of the time-varying magnetic field proximal to said detector means and resulting from the exciter means; the detector unit having a centralizer to assist in positioning the unit centrally within the pipeline;

(c) at least one processing unit housing signal processing components, the detector unit being in electrical communication with the processing unit; and (d) elongate flexible connectors spacedly interconnecting the exciter unit with the detector unit and the at least one processing unit, the elongate flexible connectors being selected to space the exciter means from the detector means a distance suitable for measurement of the remote field eddy current effect.

2. A remote field eddy current inspection device for water pipelines comprising:

(a) an exciter unit housing an exciter means for producing a time-varying magnetic field in response to an exciting signal;

(b) a first detector unit housing at least one first detector means for producing a first detecting signal representative of the time-varying magnetic field proximal to said first detector means and resulting from the exciter means;

(c) a second detector unit housing at least one second detector means for producing a second detecting signal representative of the time-varying magnetic field proximal to said second detector means and resulting from the exciter means;

(d) at least one processing unit housing signal processing components, the first and second detector units being in electrical communication with the at least one processing unit;

(e) a first elongate flexible connector spacedly connecting the exciter unit to the first detector unit, the elongate flexible connector being selected to space the exciter means from the first detector means a distance suitable for measurement of the remote field eddy current effect;

(e) a second elongate flexible connector spacedly connecting one of the exciter unit and the first detector unit to the second detector unit, the elongate flexible connector being selected to space the exciter means from the second detector means a distance suitable for measurement of the remote field eddy current effect;

(f) a third elongate flexible connector connecting the at least one processing unit to at least one of the exciter unit, the first detector unit, and the second detector unit.

3. The inspection device according to claim 1 or 2, further comprising a moving means for moving the device through a pipeline.

4. The inspection device according to claim 1 or 2, further comprising transmission means connecting the device to a remote data collection means.

5. The inspection device according to claim 1 or 2, further comprising memory components for collecting data from the device.

6. The inspection device according to claim 1 or 2, further comprising a lead unit connected at an end of the device via an elongate flexible connector, the lead unit for first encountering snags and blockages in the pipeline.

7. The inspection device according to claim 1, further comprising at least one centralizer for urging at least one of the exciter unit and the detector unit toward the axial centre of the pipeline.

8. The inspection device according to claim 2, further comprising at least one centralizer for urging at least one of the exciter unit, the first detector unit and the second detector unit toward the axial centre of the pipeline.

9. The inspection device according to claim 7 or 8, wherein the centralizer is formed as a loop of polymeric material extending from a position adjacent the leading edge of the unit to which it is attached to a position adjacent the trailing edge of the unit to which it is attached.

10. The inspection device according to claim 1 or 2, wherein the exciter means comprises a full circumferential, axial coil.

11. The inspection device according to claim 1 or 2, wherein the exciter means comprises at least one spot coil.

12. The inspection device according to claim 1 or 2, wherein the device further includes a battery.

13. The inspection device according to claim 1 or 2, wherein power is applied to the device from a remote power source connected to the device via a wireline.

14. The inspection device according to claim 1, wherein the detector means comprises at least one full circumferential, axial coil.

15. The inspection device according to claim 1, wherein the detector means comprises a solid state detector.

16. The inspection device according to claim 1, wherein the detector means comprises at least one spot coil.

17. The inspection device according to claim 16, wherein the spot coil is a coil having a U-shaped core.

18. The inspection device according to claim 17, wherein the coil is shielded.

19. The inspection device according to claim 16, wherein the spot coil is D-shaped.

20. The inspection device according to claim 16, wherein the spot coil is a coil having a read-head type (core.

21. The inspection device according to claim 17, 19 or 20, wherein the core includes a high-$\mu$ material.

22. The inspection device according to claim 16, wherein the spot coil is a coil having a core containing particles of high-$\mu$, electrically conductive material, the particles having electrically insulative material disposed therebetween.

23. A remote field eddy current inspection device for water pipelines comprising:
(a) an exciter unit housing an exciter means for producing a time-varying magnetic field in response to an exciting signal;
(b) a first detector unit housing at least one first detector means for producing a first detecting signal representative of the time-varying magnetic field proximal to said first detector means and resulting from the exciter means;
(c) a second detector unit housing at least one second detector means for producing a second detecting signal representative of the time-varying magnetic field proximal to said second detector means and resulting from the exciter means;
(d) an elongate flexible connector spacedly connecting the exciter unit to the first detector unit, the elongate flexible connector being selected to space the exciter means from the first detector means a distance suitable for measurement of the remote field eddy current effect;
(e) an elongate flexible connector spacedly connecting one of the exciter unit and the first detector unit to the second detector unit, the elongate flexible connector being selected to space the exciter means from the second detector means a distance suitable for measurement of the remote field eddy current effect,
wherein the detector means includes an outer ring of spot coils disposed to measure the radial component of the magnetic field and an inner ring of spot coils disposed to measure the radial component of the magnetic field, the rings of coils being positioned at substantially the same position along the axis of the device and the outer ring of coils being disposed between an outer wall of the device and the inner ring of coil, each coil in the outer ring of coils being positioned such that its axis is substantially aligned with the axis of one coil from the inner ring of coils.

24. The inspection device according to claim 2, wherein the detector means in each of the first detector unit and the second detector unit comprises at least one axial coil.

25. The inspection device according to claim 1 or 2, wherein the elongate flexible connector comprises flexible, tubular construction.

26. The inspection device according to claim 1 or 2, wherein the elongate flexible connector comprises a shaft having at least one pivotally moveable joint therealong.

27. The inspection device according to claim 26 wherein the pivotally moveable joint is a universal joint.

28. The inspection device according to claim 1 or 2, further comprising a trailing unit flexibly connected to the unit positioned last.

29. The inspection device according to claim 5, wherein the memory components comprise a battery, a memory unit, and at least one of (i) a timer and (ii) a displacement sensor.

30. The inspection device according to claim 3 wherein the moving means includes a pulling cable connected to a pulling means.

31. The inspection device according to claim 3 wherein the moving means includes a pulling pig.

32. An inspection device as claimed in claim 1 wherein the distance between said detector means and said exciter means is at least two times the diameter of the pipeline being inspected.

33. An inspection device as claimed in claim 2 wherein the distance between said first detector means and said exciter means at least about two times the diameter of the pipeline being inspected.

34. An inspection device as claimed in claim 1 or 2, further comprising a device locating means for determining the position of the device.

35. An inspection device as claimed in claim 34 wherein said device locating means comprises a displacement sensor coupled to a wireline connected to said inspection device wherein said displacement sensor produces an output representative of the movement of said wireline.

36. A remote field eddy current method for inspecting water pipelines comprising:
(a) moving an inspection device through pipeline using a moving means, wherein the inspection device includes an exciter unit housing an exciter means, a detector unit housing at least one detector means, a processing unit housing processing components, and elongate flexible connectors spacedly connecting the exciter unit with the detector unit and the processing unit, the elongate flexible connectors being selected to space the exciter means from the detector means a distance suitable for measurement of the remote field eddy current effect; the detector unit having a centralizer to position the unit centrally within the pipeline;
(b) inducing a time-varying magnetic field in the pipeline with the exciter means in response to an exciting signal;

(c) producing a detecting signal representative of the magnetic field proximal to the detector means and resulting from the exciter means;

(d) producing data representative of the detecting signal.

37. The inspection method according to claim 36, further comprising transmitting the data to a remote surface data collection unit.

38. The inspection method according to claim 36 further comprising storing the data in a memory collection unit connected to the detector unit.

39. The inspection method according to claim 36, wherein moving comprises pulling the inspection device through the system using a pulling line attached to a pulling means.

40. The inspection method according to claim 36, wherein moving comprises pulling the inspection device through the system using a pulling pig.

41. The inspection method according to claim 36 wherein said data is encoded into a digital data stream representative of said data.

42. The inspection method according to claim 41 wherein the inspection device further includes storage means for storing said digital data.

43. The inspection method according to claim 36, further comprising a device locating means for determining the position of the device.

44. The inspection method according to claim 43 wherein said device locating means comprises a displacement sensor coupled to a wireline connected to said inspection device wherein said displacement sensor produces an output representative of the movement of said wireline.

45. The inspection method according to claim 36 wherein the data is manipulated to produce an output signal representative of at least one of:

(i) a phase difference between the exciting signal and the detecting signal;

(ii) a ratio of the detecting signal and the exciting signal;

(iii) an in-phase component of the detecting signal with reference to the exciting signal; and (iv) an quadrature component of the detecting signal with reference to the exciting signal.

46. The inspection method according to claim 36 wherein the device further includes a second detector unit housing at least one second detector means for producing a second detecting signal representative of the time-varying magnetic field proximal to said second detector means and resulting from the exciter means and an elongate flexible connector spacedly connecting one of the exciter unit and the detector unit to the second detector unit, the elongate flexible connector being selected to space the exciter means from the second detector means a distance suitable for measurement of the remote field eddy current effect;

and the method further comprising producing a second detecting signal representative of the magnetic field proximal to the second detector means and resulting from the exciter means; and producing data representative of the second detecting signal.

47. The inspection method according to claim 46 wherein the data is manipulated to produce an output signal representative of at least one of:

(i) the phase difference between the exciter signal and the detecting signal;

(ii) the phase difference between the exciter signal and the second detecting signal;

(iii) the phase difference between the detector signal and the second detecting signal;

(iv) a ratio of the detecting signal and the exciting signal;

(v) a ratio of the second detecting signal and the exciting signal;

(vi) a ratio of the detecting signal and the second detecting signal.

48. The inspection method according to claim 46 wherein the detecting means is an first axial coil and the second detecting means is a second axial coil.

49. The inspection method according to claim 48 wherein a differential signal is determined from the detecting signal and the second detecting signal.

50. The inspection method according to claim 45 or 47 wherein said output signal is encoded into a digital data stream representative of said output signal.

51. A remote field eddy current inspection device for water pipelines comprising:

an exciter unit housing an exciter means for producing a time-varying magnetic field in response to an exciting signal and spacedly connected thereto a detector unit housing at least one detector means for producing a detecting signal representative of the time-varying magnetic field proximal to said detector means and resulting from the exciter means, the detector means includes an outer ring of spot coils disposed to measure the radial component of the magnetic field and an inner ring of spot coils disposed to measure the radial component of the magnetic field, the rings of coils being positioned at substantially the same position along the axis of the device and the outer ring of coils being disposed between an outer wall of the device and the inner ring of coil, each coil in the outer ring of coils being positioned such that its axis is substantially aligned with the axis of one coil from the inner ring of coils.

52. The inspection device as claimed in 52 further comprising a means for determining a differential signal from any of the coils having their axis aligned.

53. The inspection device as claimed in 52 wherein the means is a differential connection between the coils.

54. The inspection device as claimed in 52 wherein the means is an algorithm for differentially comparing detecting signals generated by the coils.

* * * * *

UNITED STATES PATENT AND TRADEMARK OFFICE
CERTIFICATE OF CORRECTION

PATENT NO. : 6,087,830
DATED : July 11, 2000
INVENTOR(S) : Brandly et al.

Page 1 of 2

It is certified that error appears in the above-identified patent and that said Letters Patent is hereby corrected as shown below:

| Column | Line | Error |
|---|---|---|
| [56] Pg. 2, col. 2 | Refs. Cited (Other Publs., Item 4) | "or" should read --of-- |
| 19 (Claim 20, | 36 line 2) | delete "(" before "core" |
| 19 (Claim 23, | 63 line 20) | after "effect;" insert --and-- |
| 20 (Claim 23, | 2 line 26) | "effect," should read --effect;-- |
| 20 (Claim 36, | 54 line 1) | after "through" insert --the-- |

UNITED STATES PATENT AND TRADEMARK OFFICE
CERTIFICATE OF CORRECTION

Page 2 of 2

PATENT NO. : 6,087,830
DATED : July 11, 2000
INVENTOR(S) : Brandly et al.

It is certified that error appears in the above-identified patent and that said Letters Patent is hereby corrected as shown below:

| Column | Line | Error |
|---|---|---|
| 21 (Claim 36, | 3 line 19) | insert --and-- after "means;" |
| 22 (Claim 48, | 18 line 1) | delete "an" and insert --a-- |

Signed and Sealed this

First Day of May, 2001

Attest:

NICHOLAS P. GODICI

Attesting Officer

Acting Director of the United States Patent and Trademark Office